(12) United States Patent
Biedermann et al.

(10) Patent No.: US 11,992,243 B2
(45) Date of Patent: May 28, 2024

(54) BONE ANCHORING DEVICE

(71) Applicant: BIEDERMANN TECHNOLOGIES GMBH & CO. KG, Donaueschingen (DE)

(72) Inventors: Lutz Biedermann, VS-Villingen (DE); Wilfried Matthis, Weisweil (DE); Martin Meer, Vöhringen (DE)

(73) Assignee: BIEDERMANN TECHNOLOGIES GMBH & CO. KG, Donaueschingen (DE)

( * ) Notice: Subject to any disclaimer, the term of this patent is extended or adjusted under 35 U.S.C. 154(b) by 0 days.

(21) Appl. No.: 17/403,343

(22) Filed: Aug. 16, 2021

(65) Prior Publication Data

US 2022/0031368 A1 Feb. 3, 2022

Related U.S. Application Data

(63) Continuation of application No. 16/552,661, filed on Aug. 27, 2019, now Pat. No. 11,123,109, which is a (Continued)

(30) Foreign Application Priority Data

Dec. 23, 2010 (EP) .................................. 10196880

(51) Int. Cl.
*A61B 17/70* (2006.01)
(52) U.S. Cl.
CPC ..... *A61B 17/7037* (2013.01); *Y10T 29/49826* (2015.01)
(58) Field of Classification Search
None
See application file for complete search history.

(56) References Cited

U.S. PATENT DOCUMENTS 6,113,601 A * 9/2000 Tatar ................... A61B 17/7037
606/272
6,248,105 B1 6/2001 Schläpfer et al.
(Continued)

FOREIGN PATENT DOCUMENTS

CN 1254266 A 5/2000
CN 101664334 A 3/2010
(Continued)

OTHER PUBLICATIONS

Extended European Search Report for European Application No. EP 10 19 6880, Extended European Search Report dated May 12, 2011 dated May 20, 2011 (6 pgs.).

*Primary Examiner* — Tessa M Matthews
(74) *Attorney, Agent, or Firm* — Lewis Roca Rothgerber Christie LLP

(57) ABSTRACT

A bone anchoring device includes an anchoring element having a shaft and a head, a receiving part having a coaxial bore and a seat for receiving the head, a pressure element configured to be movable within the bore, and a preload element being positionable between the head and the pressure element. When the head is inserted in the receiving part, the head is pivotable with respect to the receiving part, and can be locked at an angle relative to the receiving part by the pressure element. The pressure element can assume a position relative to the receiving part where the pressure element and the preload element are in direct contact, and where the pressure element exerts a force onto the head via the preload element to maintain one of a plurality of releasable angular positions between the head and the receiving part by friction before locking the head.

26 Claims, 7 Drawing Sheets

Related U.S. Application Data continuation of application No. 13/336,708, filed on Dec. 23, 2011, now Pat. No. 10,433,877.

(60) Provisional application No. 61/426,776, filed on Dec. 23, 2010.

(56) References Cited

U.S. PATENT DOCUMENTS

| | | |
|---|---|---|
| 7,001,389 B1 | 2/2006 | Navarro et al. |
| 7,867,258 B2 | 1/2011 | Drewry et al. |
| 2004/0267264 A1 | 12/2004 | Konieczynski et al. |
| 2006/0155278 A1 | 7/2006 | Warnick |
| 2006/0173456 A1 | 8/2006 | Hawkes et al. |
| 2007/0055240 A1 | 3/2007 | Matthis et al. |
| 2007/0118117 A1 | 5/2007 | Altarac et al. |
| 2008/0015597 A1 | 1/2008 | Whipple |
| 2008/0045951 A1 | 2/2008 | Fanger et al. |
| 2008/0147121 A1 | 6/2008 | Justis et al. |
| 2008/0269809 A1* | 10/2008 | Garamszegi ....... A61B 17/8605 606/301 |
| 2010/0087863 A1 | 4/2010 | Biedermann et al. |
| 2010/0160976 A1* | 6/2010 | Biedermann ...... A61B 17/7035 606/305 |
| 2011/0089755 A1 | 4/2011 | Itano et al. |
| 2011/0093021 A1 | 4/2011 | Fanger et al. |
| 2012/0046700 A1 | 2/2012 | Jackson et al. |
| 2013/0150852 A1 | 6/2013 | Shluzas et al. |
| 2013/0184766 A1 | 7/2013 | Black |
| 2021/0015521 A1 | 1/2021 | Biedermann et al. |

FOREIGN PATENT DOCUMENTS

| | | |
|---|---|---|
| JP | 2008-526435 A | 7/2008 |
| WO | WO 2006/076422 A2 | 7/2006 |
| WO | WO 2008/112114 A1 | 9/2008 |
| WO | WO 2009/132110 A1 | 10/2009 |

\* cited by examiner

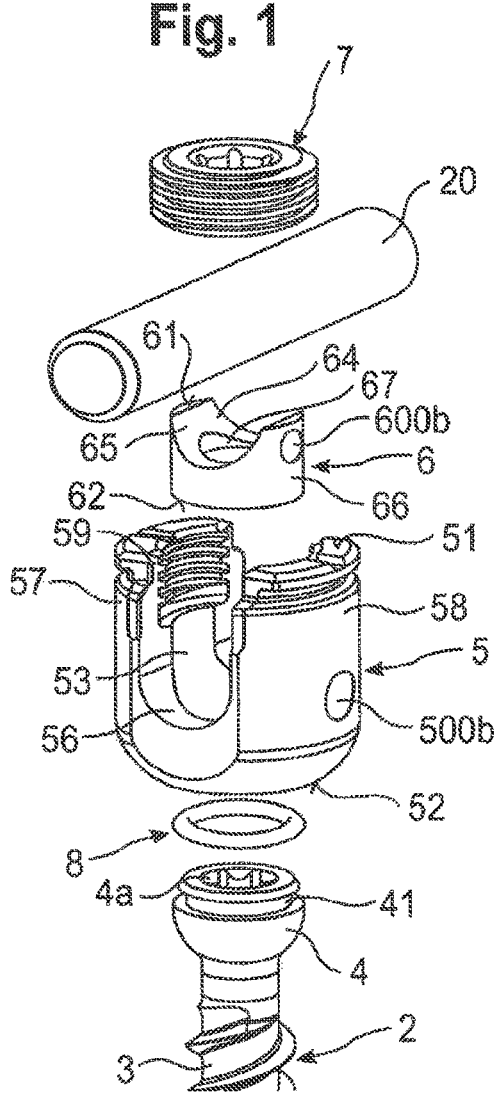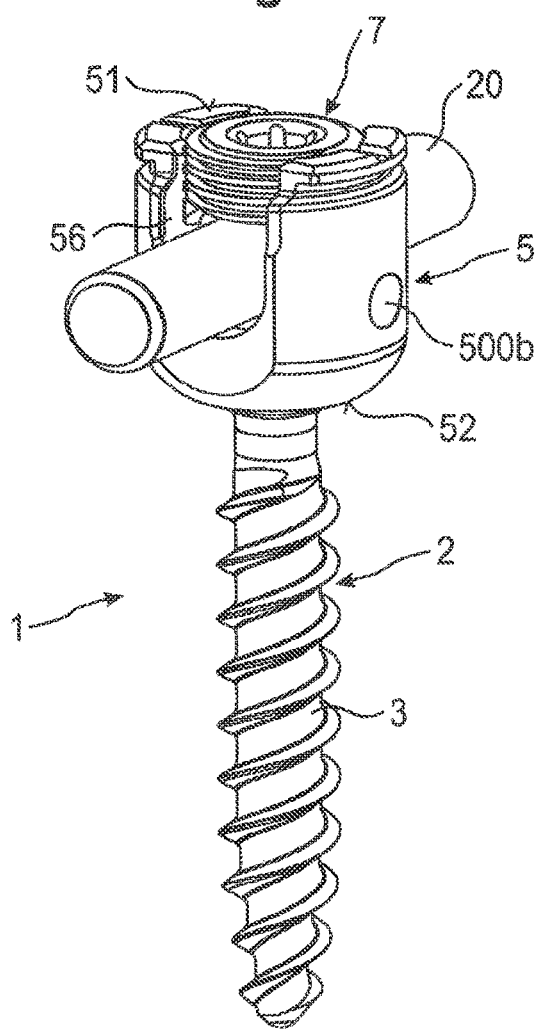

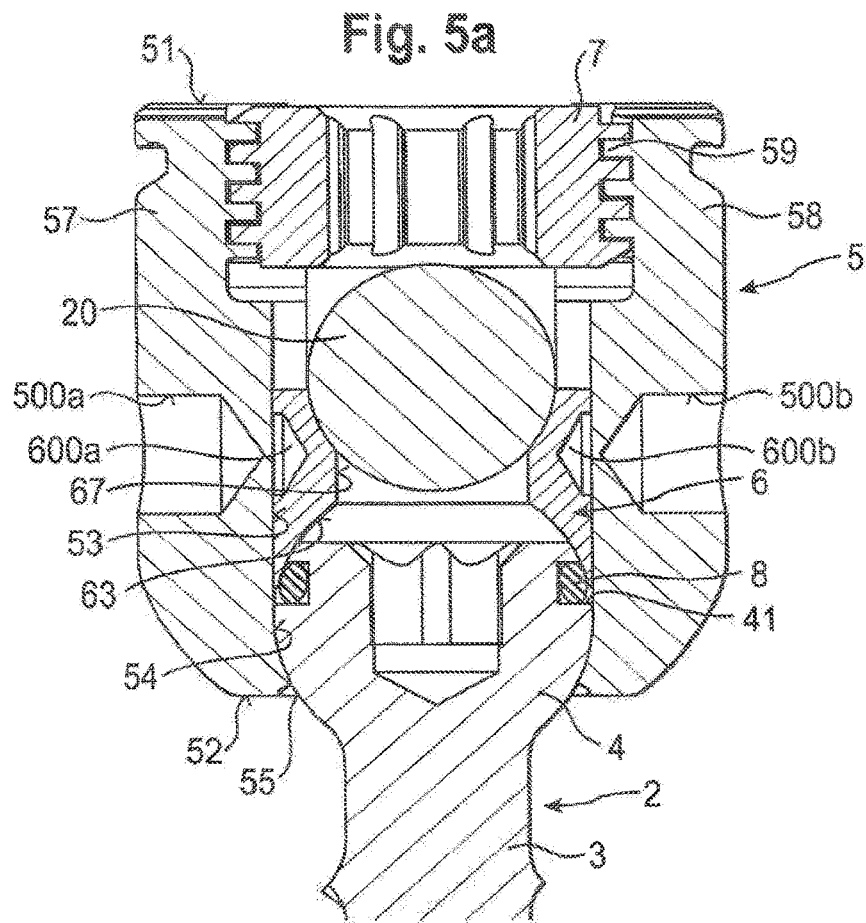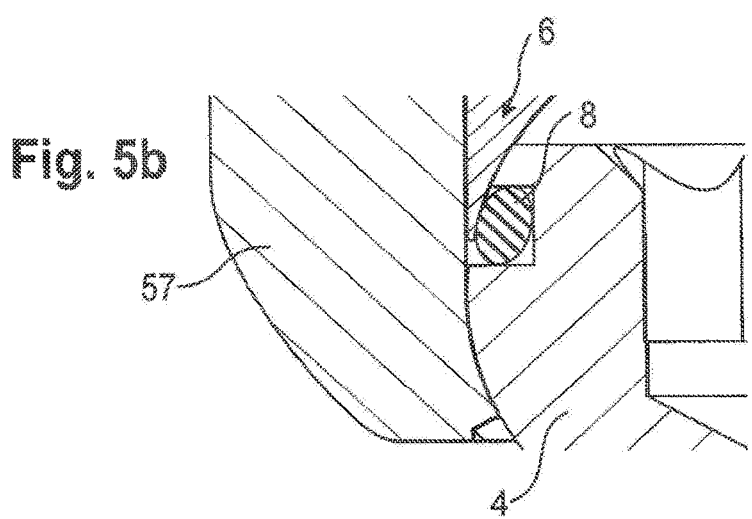

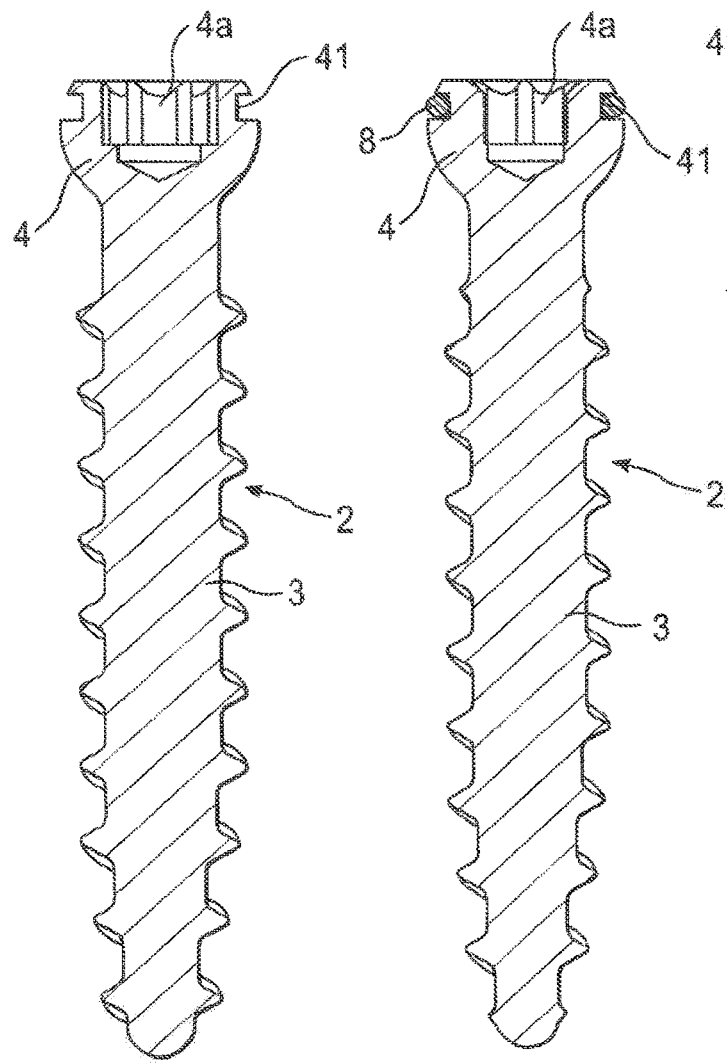

BONE ANCHORING DEVICE

CROSS-REFERENCE TO RELATED APPLICATION(S)

This application is a continuation of U.S. patent application Ser. No. 16/552,661, filed Aug. 27, 2019, which is a continuation of U.S. patent application Ser. No. 13/336,708, filed Dec. 23, 2011, now U.S. Pat. No. 10,433,877, which claims the benefit of U.S. Provisional Patent Application Ser. No. 61/426,776, filed Dec. 23, 2010, the contents of which are hereby incorporated by reference in their entirety, and claims priority to European Patent Application EP 10 196 880.8, filed Dec. 23, 2010, the contents of which are hereby incorporated by reference in their entirety.

BACKGROUND

Field of the Invention

The invention relates to a bone anchoring device for anchoring a stabilization rod to a bone or to a vertebra. The bone anchoring device includes a bone anchoring element and a receiving part for receiving a head of the bone anchoring element and for receiving a stabilization rod to be connected to the bone anchoring element. The bone anchoring element is pivotably connected to the receiving part and can be fixed at an angle by exerting pressure onto the head via a pressure element which may be arranged in the receiving part. The head has a recess which accommodates a closed ring which is configured to cooperate in such a way with the head and the pressure element that the pressure element can assume a position within the receiving part in which it clamps the head via the ring by friction without fully locking the head with respect to the receiving part.

Description of Related Art

US 2004/0267264 A1 describes a polyaxial fixation device, wherein the polyaxial bone screw includes an engagement member that is adapted to provide sufficient friction between the spherical head and the receiver member to enable the shank to be maintained in a desired angular orientation before locking the spherical head within the receiver member. The engagement member is realized, for example, by an open snap ring around the head or by spring members provided at the compression cap to frictionally engage the spherical head or by a slot provided in the compression cap.

SUMMARY

It is an object of the invention to provide a bone anchoring device which allows for improved handling during surgery and which can be manufactured cost-effectively in a simple manner.

With the bone anchoring device according to embodiments of the present invention, a temporary clamping of the head in a desired angular position with respect to the receiving part without locking the head can be achieved. This allows the receiving part to be held in an adjustable angular position. In this position the pressure element exerts a preload onto the head via the ring, such that the head is not locked but is frictionally prevented from freely pivoting. When the head is temporarily clamped, the alignment of the receiving part to the rod and the insertion of the rod is facilitated. In addition, when the rod is already inserted into the receiving part, adjustments of the rod are still possible without completely loosening the head within the receiving part. Finally, the pressure element can be pressed onto the head to lock the head in a desired portion.

In addition, the bone anchoring device has relatively few parts which are of simple design.

Furthermore, the heads of already manufactured bone anchoring devices can easily be upgraded to the system according to embodiments of the present invention. For example, in some embodiments, only a groove around the head and a closed ring which is accommodated by the groove have to be further provided.

The parts of the bone anchoring device can be manufactured in series at low costs.

BRIEF DESCRIPTION OF THE DRAWINGS

Further features and advantages of the invention will become apparent from the description of embodiments by means of the accompanying drawings. In the drawings:

FIG. 1 shows a perspective exploded view of a bone anchoring device according to an embodiment of the present invention;

FIG. 2 shows the bone anchoring device of FIG. 1 in an assembled state;

FIG. 3c shows a top view of the bone anchoring element of FIG. 3a;

FIG. 4b shows a side view of the ring of FIG. 4a;

FIG. 4c shows a cross-sectional view of the ring of FIG. 4a;

FIG. 4d shows a top view of the ring of FIG. 4a;

FIG. 5a shows a cross-sectional view of the bone anchoring device of FIGS. 1 and 2 in an assembled state before final locking of a head of a bone anchoring element;

FIG. 5b shows an enlarged portion of FIG. 5a;

FIG. 6a shows a cross-sectional exploded view of a bone anchoring element and a ring according to an embodiment of the present invention;

FIG. 6b shows a cross sectional view of the bone anchoring element and the ring of FIG. 6a in an assembled state;

FIG. 6c shows an enlarged portion of FIG. 6b;

DETAILED DESCRIPTION

Figure 3A:
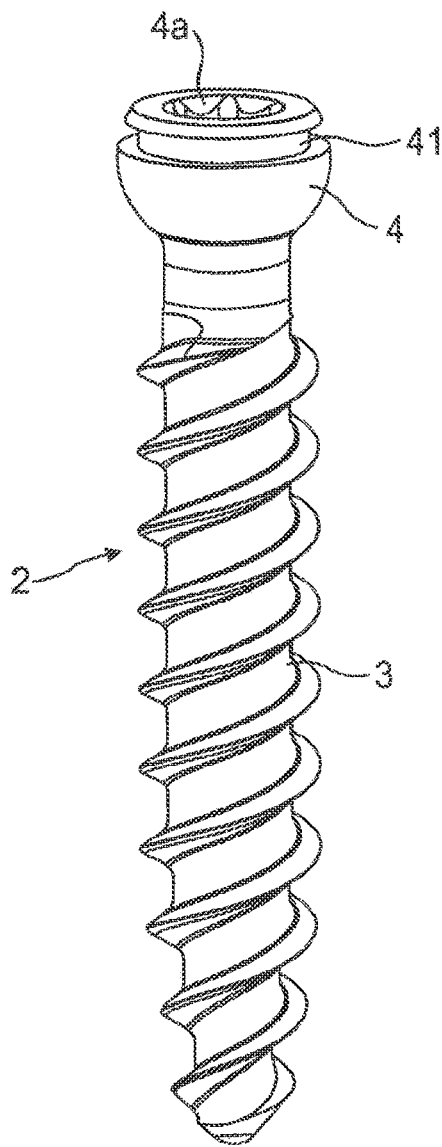
FIG. 3a shows a perspective view of a bone anchoring element according to an embodiment of the present invention.

A polyaxial bone anchoring device 1 according to a first embodiment, as shown in FIGS. 1, 2 and 5a, includes a bone anchoring element 2 in the form of a screw member having a threaded shaft 3 and a head 4. The head 4 includes a tool recess 4a at its free end for engagement with a tool (not shown) to insert the threaded shaft 3 into a bone. The bone anchoring device 1 further includes a receiving part 5 for connecting the screw member 2 to a rod 20. A pressure element 6 is arranged in the receiving part 5 on top of the head 4 (as illustrated). For securing the rod 20 in the receiving part 5 and for exerting pressure onto the head 4, a locking device, for example, an inner screw 7, which cooperates with the receiving part 5, is provided.

Figure 3B:
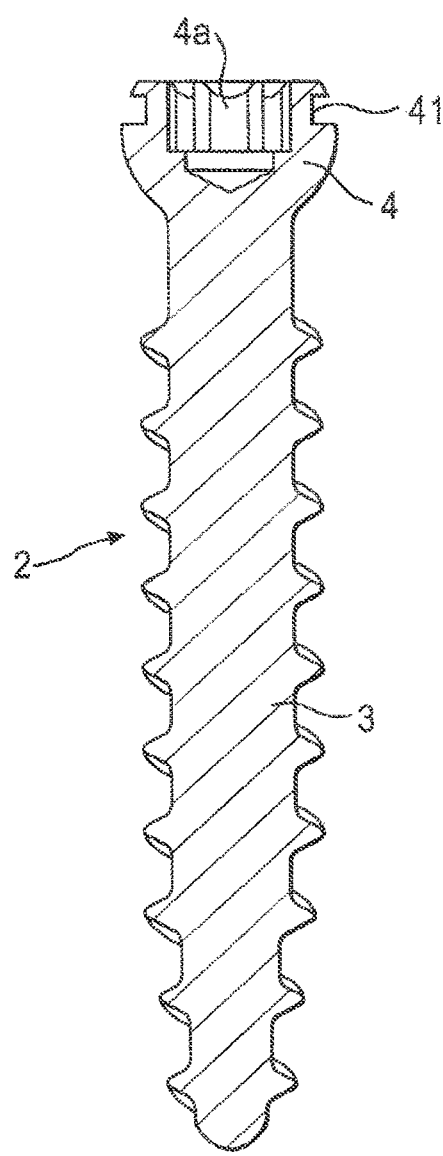
FIG. 3b shows a cross-sectional view of the bone anchoring element of FIG. 3a, the cross-section being taken in a plane containing the screw axis.
Figure 3C:
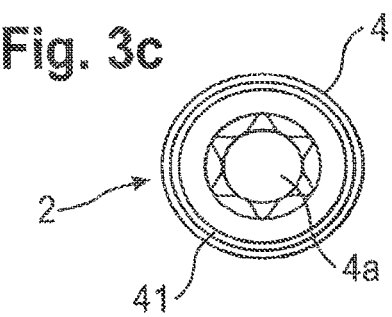

As shown in FIGS. 3a, 3b and 3c, the head 4 is shaped as a spherical segment having a flat free end and having the tool recess 4a at the flat free end. An annular groove 41 is provided at a position above a greatest diameter of the head 4 in a direction towards the free end. A cross-section of the annular groove 41 is substantially trapezoidal with an open side, as can also be seen in FIG. 6a. The annular groove 41 is configured to accommodate a ring 8. A ground or innermost surface of the annular groove 41 is substantially coaxial with an axis of the screw member 2. The edges of the ground of the annular groove 41 can be rounded. In some embodiments, the free end of the head 4 can also differ from the described flat form.

The receiving part 5 is a substantially cylindrical one-piece part, and has a top end 51 and a bottom end 52. A passageway extending from the top end 51 to the bottom end 52 is formed by a coaxial bore 53 followed by a seat portion 54 for receiving the head 4 of the screw member 2. The seat portion 54 has an opening 55 at the bottom end 52 through which the shaft 3 of the screw member 2 can extend. The seat portion 54 is shown to be spherically-shaped, but can be tapered or can have any other shape that allows receiving of the head 4 so that the head 4 can pivot with respect to the receiving part 5. At the top end 51, a substantially U-shaped recess 56 is provided by means of which two free legs 57, 58 are formed that serve as sidewalls of a channel for receiving the rod 20. An internal thread 59 is provided on the legs 57, 58 for cooperating with the inner screw 7.

The receiving part 5 also has at a position closer to the bottom end 52 than to the top end 51 two blind holes 500a, 500b forming crimp bores that extend from an outer surface of the receiving part 5 to a distance from the inner wall of the coaxial bore 53, for crimping in a manner described below. The blind holes 500a, 500b may be arranged 180° offset from each other and at 90° with respect to the channel formed by the U-shaped recess 56. The blind holes 500a, 500b are aligned perpendicular with respect to a bore axis of the coaxial bore 53. The portions of the receiving part 5 that are between the closed ends of the blind holes 500a, 500b and the coaxial bore 53 of the receiving part 5 are configured to be deformable portions.

The pressure element 6 is formed in one piece. The pressure element 6 is of substantially cylindrical construction and has an outer diameter which allows it to move in an axial direction within the bore 53 of the receiving part 5. The pressure element 6 has a top end 61 and a bottom end 62. When the pressure element 6 is inserted into the receiving part 5, the bottom end 62 faces the head 4 of an inserted bone anchoring element 2. At the top end 61, a U-shaped recess 64 is provided by means of which two free legs 65, 66 are formed, forming a channel to receive the rod 20 therein. Furthermore, the pressure element 6 includes a coaxial bore 67 for providing access to the screw head 4 with a tool (not shown). As shown in FIGS. 1 and 2, the pressure element 6 is a solid member which is arranged in the receiving part 5, such that the U-shaped recess 56 of the receiving part 5 and the U-shaped recess 64 of the pressure element 6 can be aligned.

The pressure element 6 includes two crimp bores 600a, 600b corresponding to the crimp bores 500a, 500b of the receiving part 5, wherein after crimping, the pressure element 6 may be held in a rotationally aligned position and at an axial position in which the pressure element 6 can exert a slight preload onto the head 4.

Figure 4A:
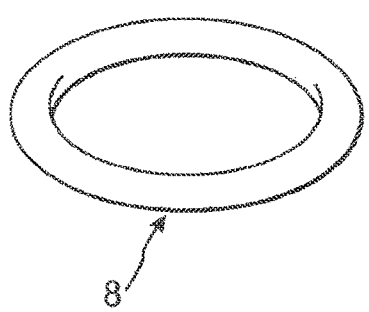
FIG. 4a shows a perspective view of a ring according to an embodiment of the present invention.
Figure 4B:
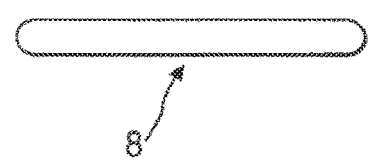
Figure 4C:
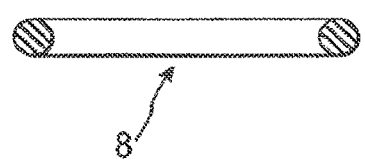
Figure 4D:
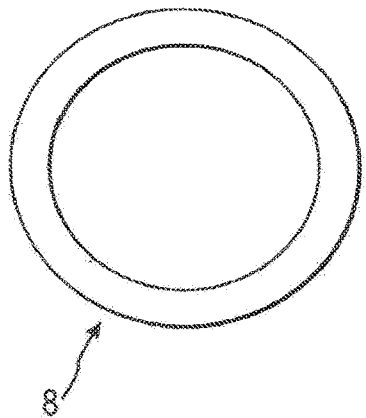

FIGS. 4a to 4d show a ring 8 according to an embodiment of the present invention. As shown in FIG. 4c the ring 8 is closed, and has a substantially circular cross-section in an undeformed state. The ring 8 may be made of a plastic material which is elastically deformable, for example a bio-compatible elastomer. As an elastomer, for example, UHMWPE (Ultra-high-molecular-weight polyethylene), Silicon, PCU, SIBS, or combinations thereof can be used. Other parts of the bone anchoring device 1 may be made of a body-compatible material, such as a body-compatible metal, for example, titanium, body-compatible metal alloys such as, for example, Nitinol, or from a body-compatible plastic material, such as, for example, PEEK, or combinations thereof.

The size of the ring 8 is such that when the ring 8 is inserted into the annular groove 41, the ring 8 is substantially undeformed and projects slightly out of the annular groove 41. Since the cross-section of the annular groove 41 is trapezoidal, the annular groove 41 provides space for the deformation of the ring 8 upon exertion of a load onto the ring 8 by the pressure element 6 (e.g., from above).

Figure 7:
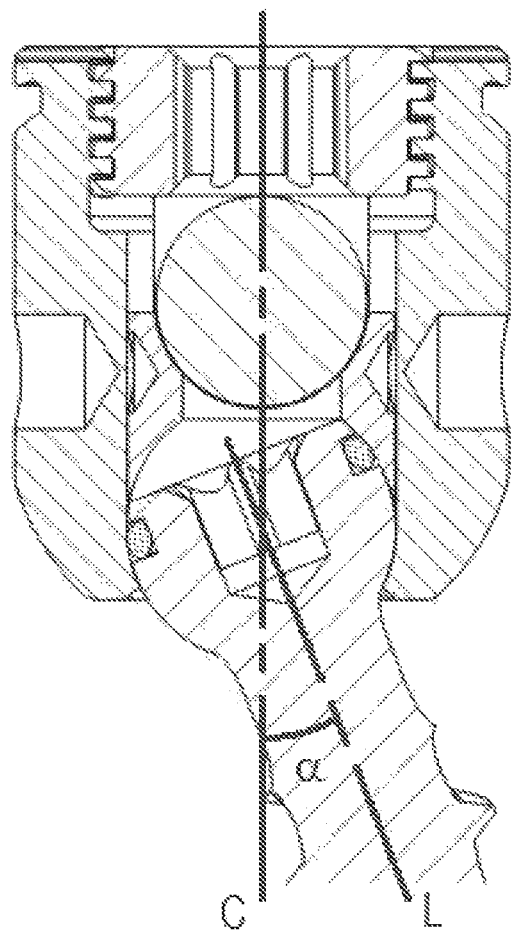
FIG. 7 shows a cross-section view of the bone anchoring device in an assembled state, according to an embodiment of the present invention.

In an assembled state, as shown in FIG. 5a, the head 4 is located in the seat 54 and the pressure element 6 is arranged on top of the head 4. The heights of the free legs 65, 66 of the pressure element 6 are configured such that the free legs 65, 66 do not extend above the rod 20 when the rod 20 is inserted and rests on the bottom of the channel of the pressure element 6. The pressure element 6, as shown in FIGS. 5a and 5b, can assume a first position which is defined by connecting the pressure element 6 and the receiving part 5 by crimping through the crimp bores 500a, 500b, and in some cases, 600a, 600b. In this manner, the ring 8 and the pressure element 6 cooperate in such a way that the pressure element 6 exerts a preload force onto the head 4 via the ring 8, where the head 4 may be maintained at an angular position by friction before finally locking the head 4. An example of such an angular position is shown in FIG. 7, where an angle α is formed between a longitudinal axis L of the bone anchoring element and a central axis C of the receiving part. The force may be exerted onto the head 4 via the inner screw 7, the rod 20, the pressure element 6, and the ring 8. The ring 8, which has a substantially circular cross-section, may be deformed such that its cross-section is substantially oval in this first position. By the deformation, the ring 8 exerts a counter force onto the pressure element 6 so that the head 4 is maintained in an angular position. This position can be adjusted by applying a force to the bone anchoring element 2 or the receiving part 5 to overcome the friction force. The pressure element 6 can also assume a second position in which the head 4 is locked by further screwing in the inner screw 7. Furthermore, the pressure element 6 can assume third positions in which the head 4 is capable of freely pivoting. In the third position, the pressure element 6 is substantially not in frictional contact with the ring 8. By selecting the size of the ring 8 and the size of the annular groove 41, a desired friction force can be achieved.

Figure 6D:
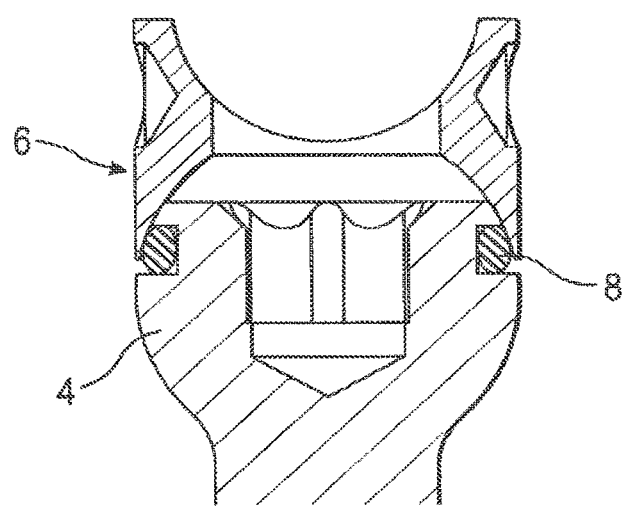
FIG. 6d shows a cross sectional view of the bone anchoring element and the ring of FIG. 6a and a pressure element in an assembled state according to an embodiment of the present invention.

FIGS. 6a to 6d show the assembly of the bone anchoring element 2 with the ring 8. The ring 8 is mounted on the head 4 of the bone anchoring element 2 and is accommodated by the annular groove 41, as shown in FIGS. 6b and 6c. FIG. 6d shows the bone anchoring element 2 with a mounted pressure element 6. When moving the pressure element 6 downwards in a direction towards the shaft 3, the head 4 may be maintained at an angular position by friction.

In use, first, the bone anchoring device 1 may be provided in a pre-assembled state, with the pressure element 6 being in the first position in which the head 4 is temporarily frictionally clamped. Usually several bone anchoring devices 1 are utilized. The screw members 2 are then screwed into respective bones or vertebrae, and then the corresponding receiving parts 5 are pivoted by applying a force to overcome the clamping force, until each receiving part 5 has a desired orientation for insertion of the rod 20. Due to the temporary clamping, the receiving parts 5 are held in their respective angular positions. The rod 20, which connects the bone anchoring devices 1, is inserted and the inner screws 7 are tightened to move the pressure elements 6 downwards to lock the heads 4 so that the angular positions of the screw members 2 with respect to the receiving parts 5 are fixed. The rod 20 is then also fixed by the inner screws 7.

For the bone anchoring element, various different kinds of anchoring elements can be used and combined with the receiving part. These anchoring elements may include, for example, screws with different length, screws with different diameters, cannulated screws, screws with different thread forms, nails, etc. In some embodiments, the head and the shaft can also be separate parts which can be connected to each other.

Various kinds of receiving parts can also be used, in particular, receiving parts with different locking devices. For example, instead of using a one-part locking device such as the inner screw which locks the rod and the head simultaneously, two-part locking devices with an outer screw and an inner screw can be used. In this case the pressure element may have a U-shaped recess with legs extending above the rod. With the two-part locking device, the head and the rod can be fixed independently. Further, outer nuts, outer caps, bayonet locking devices, or various other kinds of locking devices can also be utilized. The shape of the receiving part is also not limited to the embodiment shown. For example, the receiving part can have an asymmetric end portion for allowing a greater pivot angle of the screw member to one side.

In a modified embodiment, the annular groove is not provided on the head, but rather on the inner wall of the receiving part or on the pressure element, for accommodating the ring. The ring and the head may cooperate in such a way that the pressure element exerts a preload force onto the head via the ring, where the head is maintained at an angular position by friction before finally locking the head 4.

In a further modification, a ring is provided which is made of a non-flexible material, such as PEEK, for example. Such a ring should only be slightly oversized with respect to the surface of the head, to ensure the frictional contact. Further, the ring's cross-section can also be substantially oval, rectangular, etc., or can also vary over the circumference of the ring.

It is also possible to use one or several flexible elements which are arranged in the annular groove of the head or the pressure element, instead of using one single ring. The cross-sections of these elements or the ring, respectively, may also vary.

In a further modification, the receiving part may be configured to allow the introduction of the bone anchoring element from the bottom end.

While the present invention has been described in connection with certain exemplary embodiments, it is to be understood that the invention is not limited to the disclosed embodiments, but is instead intended to cover various modifications and equivalent arrangements included within the spirit and scope of the appended claims, and equivalents thereof.

What is claimed is:

1. A bone anchoring device comprising:
an anchoring element having a shaft for anchoring in a bone and a head;
a receiving part having a first end and a second end, a recess for receiving a rod, a bore extending from the first end in the direction of the second end and configured to pivotably receive the head near the second end;
a pressure element movable in the bore to directly engage and exert pressure on the head for locking an angle of the head relative to the receiving part; and
a ring that is radially expandable and compressible;
wherein when the head, the pressure element, and the ring are assembled to the receiving part, the pressure element is movable axially relative to the receiving part and the ring, while a central axis of the pressure element is substantially fixed relative to a central axis of the receiving part such that the pressure element is pivotable together with the receiving part relative to the head when in contact with the head;
wherein at least when a shaft axis of the anchoring element is coaxial with the central axis of the receiving part, the pressure element is movable from a first axial position where the ring has a first outer width, to a second axial position where the pressure element engages and adjusts the ring to have a second outer width different from the first outer width to hold a position of the head relative to the receiving part, and wherein when the pressure element is at the second axial position, at least part of the pressure element is at a same axial height as at least part of the ring to restrict the outer width of the ring from returning to the first outer width.

2. The bone anchoring device of claim 1, wherein the pressure element is a monolithic part.

3. The bone anchoring device of claim 1, wherein the ring is a closed ring.

4. The bone anchoring device of claim 1, wherein the ring comprises a polymer material.

5. The bone anchoring device of claim 1, wherein when the pressure element is at the second axial position, the ring is configured to contact the head.

6. The bone anchoring device of claim 1, wherein when the pressure element is at the second axial position, the pressure element restricts expansion of the ring.

7. The bone anchoring device of claim 1, wherein the second outer width is smaller than the first outer width.

8. The bone anchoring device of claim 1, wherein the pressure element exerts an axial pressure directed towards the second end of the receiving part on the ring when the pressure element is moved from the first axial position to the second axial position.

9. The bone anchoring device of claim 1, wherein the pressure element compresses the ring radially inwardly when the pressure element is moved from the first axial position to the second axial position.

10. The bone anchoring device of claim 1, wherein an axial position of the ring relative to the receiving part remains constant when the pressure element is moved from the first axial position to the second axial position.

11. The bone anchoring device of claim 1, wherein the receiving part and the head are polyaxially adjustable relative to one another.

12. The bone anchoring device of claim 11, wherein when the pressure element is at the second axial position, the head is held at a temporary angular position relative to the receiving part.

13. The bone anchoring device of claim 1, wherein the head defines a groove.

14. The bone anchoring device of claim 13, wherein the ring is positionable in the groove.

15. The bone anchoring device of claim 1, wherein the ring is positionable in a groove that is formed on one of the receiving part or the pressure element.

16. The bone anchoring device of claim 1, wherein the pressure element is configured to be positioned at a same axial height as a majority of the ring.

17. A bone anchoring device comprising:
an anchoring element having a shaft for anchoring in a bone, the shaft having a shaft axis, and a head above the shaft, the head comprising a spherical segment-shaped outer surface that includes a greatest diameter of the sphere when measured in a direction perpendicular to the shaft axis, and a groove that extends circumferentially around the entire spherical segment-shaped outer surface, wherein the entire groove is positioned axially above the greatest diameter of the sphere on a side of the head opposite the shaft, and wherein the groove includes a first surface that is angled arranged at a non-zero angle relative to the shaft axis to face at least partially towards a free end of the head and a second surface that is arranged at a non-zero angle relative to the shaft axis to face at least partially away from the free end of the head;
a receiving part having a first end and a second end below the first end, a recess for receiving a rod, a bore extending from the first end in the direction of the second end and configured to pivotably receive the head near the second end; and
a pressure element movable in the bore for exerting pressure on the head to lock an angle of the head relative to the receiving part;
wherein when the head and the pressure element are assembled to the receiving part, the pressure element is configured to simultaneously engage an entire circumference of the groove.

18. The bone anchoring device of claim 17, wherein a ring is positionable in the groove and configured to project out of the groove to engage with at least one of the receiving part or the pressure element.

19. The bone anchoring device of claim 17, wherein the pressure element is configured to engage the entire circumference of the groove when the shaft assumes a first angular position relative to the receiving part, and is configured to disengage from at least part of the entire circumference of the groove when the shaft assumes an angular position different from the first angular position relative to the receiving part.

20. The bone anchoring device of claim 17, wherein a central axis of the pressure element is substantially fixed relative to a central axis of the receiving part such that the pressure element is pivotable together with the receiving part relative to the head when in contact with the head in the receiving part.

21. A bone anchoring device comprising:
an anchoring element having a shaft for anchoring in a bone, the shaft having a shaft axis, and a head above the shaft, the head comprising a spherical segment-shaped outer surface that includes a greatest diameter of the sphere when measured in a direction perpendicular to the shaft axis;
a receiving part having a first end and a second end, a recess for receiving a rod, a bore extending from the first end in the direction of the second end and configured to pivotably receive the head near the second end;
a pressure element movable in the bore for exerting pressure on the head to lock an angle of the head relative to the receiving part, wherein a central axis of the pressure element is substantially fixed relative to a central axis of the receiving part such that the pressure element is pivotable together with the receiving part relative to the head when in contact with the head in the receiving part; and
a ring that is radially expandable and compressible, wherein the ring is positionable in a groove formed on one of the receiving part or the pressure element;
wherein when the head, the pressure element, and the ring are assembled to the receiving part and the shaft axis is coaxial with the central axis of the receiving part, the ring is configured to directly engage the head, and the entire ring is positioned axially above the greatest diameter of the sphere on a side of the head opposite the shaft and is restricted by the groove from moving axially towards the second end of the receiving part.

22. The bone anchoring device of claim 21, wherein the groove is formed on the pressure element.

23. The bone anchoring device of claim 21, wherein the groove further restricts axial movement of the ring towards the first end of the receiving part.

24. The bone anchoring device of claim 21, wherein the ring contacts the head at a same axial height as an axial height of at least part of the groove.

25. The bone anchoring device of claim 21, wherein the pressure element is configured to directly engage the head in the receiving part.

26. The bone anchoring device of claim 21, wherein the ring is further configured to directly engage both the receiving part and the pressure element.

* * * * *

UNITED STATES PATENT AND TRADEMARK OFFICE
CERTIFICATE OF CORRECTION

PATENT NO. : 11,992,243 B2
APPLICATION NO. : 17/403343
DATED : May 28, 2024
INVENTOR(S) : Lutz Biedermann et al.

It is certified that error appears in the above-identified patent and that said Letters Patent is hereby corrected as shown below:

In the Specification

In Column 2, Line 57, after "invention." insert -- FIG. 8a shows a cross-sectional view of a bone anchoring device in an assembled state, according to a first alternative embodiment.
FIG. 8b shows a cross-sectional view of a bone anchoring device in an assembled state, according to a second alternative embodiment. -- as new paragraphs.

In Column 5, Line 44, delete "part" and insert -- part (see, e.g., Fig. 8a) --.

In Column 5, Line 44, delete "element," and insert -- element (see, e.g., Fig. 8b), --.

In Column 7, Line 27, in Claim 17, after "is" delete "angled".

Signed and Sealed this
Seventeenth Day of September, 2024

Katherine Kelly Vidal
*Director of the United States Patent and Trademark Office*